United States Patent
Blom

(10) Patent No.: US 7,856,983 B2
(45) Date of Patent: Dec. 28, 2010

(54) SPEAKING VALVE

(75) Inventor: Eric D. Blom, Carmel, IN (US)

(73) Assignee: Hansa Medical Products, Inc., Indianapolis, IN (US)

( * ) Notice: Subject to any disclaimer, the term of this patent is extended or adjusted under 35 U.S.C. 154(b) by 732 days.

(21) Appl. No.: 11/872,243

(22) Filed: Oct. 15, 2007

(65) Prior Publication Data

US 2009/0095302 A1 Apr. 16, 2009

(51) Int. Cl.
*A61M 11/00* (2006.01)
(52) U.S. Cl. .............................. 128/207.16; 128/207.14
(58) Field of Classification Search ............ 128/200.24, 128/200.26, 207.14–207.18, 207.29, 912; 604/264
See application file for complete search history.

(56) References Cited

U.S. PATENT DOCUMENTS

| | | | |
|---|---|---|---|
| 4,459,984 A | | 7/1984 | Liegner |
| 4,627,433 A | * | 12/1986 | Lieberman ............. 128/207.16 |
| 5,056,515 A | * | 10/1991 | Abel ..................... 128/207.15 |
| 5,189,534 A | | 2/1993 | McDonnell et al. |
| 5,771,888 A | * | 6/1998 | Keim .................... 128/207.15 |
| 5,806,515 A | | 9/1998 | Bare et al. |
| 5,957,978 A | | 9/1999 | Blom |
| 6,189,534 B1 | | 2/2001 | Zowtiak et al. |
| 6,588,428 B2 | | 7/2003 | Shikani et al. |
| 6,722,367 B1 | | 4/2004 | Blom |
| 2007/0144526 A1 | | 6/2007 | Blom et al. |

OTHER PUBLICATIONS

"Montgomery Tracheostomy Speaking Valve", Boston Medical Products brochure, p. 5, date unknown.
"Speaking Valves, Montgomery Tracheostomy Speaking Valve", Boston Medical Products brochure, p. 6, date unknown.
"TRACOE PhonAssist/Speaking Valve", Boston Medical Products brochure, p. 6, date unknown.
Accessories, p. 10, paragraphs A and B.
Shiley Phonate Speaking Valve, Nellcor Solutions for Patient Care brochure, Nellcor Puritan Bennett Inc., 2005.

(Continued)

*Primary Examiner*—Steven O Douglas
(74) *Attorney, Agent, or Firm*—Barnes & Thornburg LLP

(57) ABSTRACT

Apparatus for assisting phonation in a wearer of a tracheostomy tube having a first end lying outside the trachea of the wearer in the use orientation, a second end lying inside the trachea of the wearer in the use orientation, and a first lumen coupling the first and second ends of the tracheostomy tube. The tracheostomy tube may or may not include a fenestration through a sidewall of the tracheostomy tube coupling the first lumen to the outside of the tracheostomy tube. The apparatus includes a cannula for insertion into the first lumen from the first end of the tracheostomy tube. The cannula includes a first end lying outside the first end of the tracheostomy tube in the use orientation, a second, opposite end, and a second lumen coupling the first and second ends of the cannula. If the tracheostomy tube has a fenestration, the second end may lie within the first lumen adjacent and toward the first end of the tracheostomy tube from the fenestration, or generally between the first end of the tracheostomy tube and the fenestration, or adjacent the second end of the tracheostomy tube. A one-way valve is provided at the second end of the cannula.

4 Claims, 5 Drawing Sheets

OTHER PUBLICATIONS

Passy-Muir Tracheostomy & Ventilator Swallowing and Speaking Valve, 3 pages, www.passy-muir.com.
"Shiley Cuffless Tracheostomy Tubes. In the long run, the best solution for long-term care", Mallinckrodt Medical, date unknown.
Tracheostomy and Laryngectomy Tubes, Pilling Co., 1 page, date unknown.
Pilling Shikani-French Speaking Valve (Product No. 51-8090) Instructions for Use, Pilling, Rev. B-2/00, 2 pages, date unknown.
International Search Report dated Feb. 4, 2009 from PCT/US2008/072900.
International preliminary report on patentability dated Apr. 29, 2010 from PCT/US2008/072900.

* cited by examiner

SPEAKING VALVE

FIELD OF THE INVENTION

This invention relates to speech aids for tracheotomized individuals.

BACKGROUND OF THE INVENTION

It is necessary during the course of treatment of certain diseases and during certain procedures to provide tracheotomies on the individuals afflicted with such diseases, or on whom such procedures are to be performed or are being performed. In many cases, the tracheotomies remain patent for extended time periods, making it necessary and/or desirable to provide devices which permit such tracheotomized individuals to speak. While some individuals are able and willing to occlude the outer ends of their tracheotomy tubes with a finger tip when they want to speak, many individuals are not.

Some devices which perform the occlusion function are known. There is, for example, the Tucker speaking valve for use with the Jackson tracheostomy tube. Additionally, there are a number of one-way valves available from various sources that fit onto the outer ends of standard size tracheostomy tubes. These one-way valves close when pressure in the individual's trachea rises to so-called "speaking" pressure, redirecting air from the tracheostomy tube upward through the larynx, permitting phonation. Such one-way valves include, for example: the valve described in U.S. Pat. No. 6,588,428; the Montgomery( tracheostomy speaking valve (product code 221201) and TRACOE® PhonAssist speaking valve (product code 650-T), both available from Boston Medical Products; the Hood speaking valve (code SPV-3015) and Medin low resistance speaking valve (code SPV-2055), both available from Hood Laboratories, 575 Washington Street, Pembroke, Mass. 02359; the Shiley Phonate® speaking valve (product designation SSVO) available from Nellcor Puritan-Bennett LLC; and, the Passy-Muir tracheostomy & ventilator swallowing and speaking valve (PMV 005) available from Passy-Muir Inc. These valves are generally of a similar size and configuration designed to slide onto the standard 15 mm external (ventilator) end of a tracheostoma tube or cannula. The teachings of these references are hereby incorporated herein by reference. This listing is not intended to be a representation that a complete search of all relevant art has been made, or that no more pertinent art than that listed exists, or that the listed art is material to patentability. Nor should any such representation be inferred.

Problems arise with a valve such as the Tucker speaking valve in which the flapper of the valve is positioned midway along the length of the Tucker speaking valve's inner cannula. First, the flapper is oriented such that it lies at an angle across the inner cannula. This orientation provides areas in which secretions can become lodged, interfering with the normal function of the valve's flapper and adversely affecting the wearer's ability to speak while wearing it. Further, because the Tucker speaking valve, like the Jackson tracheostomy tube, is made of metal (specifically a silver alloy), the valve is heavy and expensive. Additionally, the valve leaks whether it is in the closed (non-speaking) or open (speaking) orientation.

The major problem with one-way valves that are designed to fit onto the outer ends of standard size tracheostomy tubes is that they project out quite far from the neck of the wearer when they are installed on the outer end of the tube. The bodies of most of these are in the range of 0.75 inch (about 19 mm) long and are designed to slide over the outer end of an inner cannula, which outer end itself projects about 0.75 inch (about 19 mm) beyond the outer (ventilator) end of an outer cannula or tracheostomy tube. This results in an assembly that extends forward not uncommonly 1-1.75 inch (about 2.5-4.4 cm) or so. Not surprisingly, the tracheostomy tube wearer would prefer not to have an additional 1-1.75 inch (about 2.5-4.4 cm) or so apparatus projecting out from his or her neck in order to be able to speak without having to occlude the outer end of his or her tracheostomy tube each time he or she wanted to say something.

DISCLOSURE OF THE INVENTION

According to an aspect of the invention, apparatus is provided for assisting phonation in a wearer of a tracheostomy tube having a first end lying outside the trachea of the wearer in the use orientation, a second end lying inside the trachea of the wearer in the use orientation, a first lumen coupling the first and second ends of the tracheostomy tube and a fenestration through a sidewall of the tracheostomy tube coupling the first lumen to the outside of the tracheostomy tube. The apparatus includes a cannula for insertion into the first lumen from the first end of the tracheostomy tube. The cannula includes a first end lying outside the first end of the tracheostomy tube in the use orientation, a second end lying within the first lumen adjacent the fenestration, and a second lumen coupling the first and second ends of the cannula.

Illustratively, in the use orientation, the second end of the cannula lies toward the first end of the tracheostomy tube from the fenestration.

According to another aspect of the invention, apparatus is provided for assisting phonation in a wearer of a tracheostomy tube having a first end lying outside the trachea of the wearer in the use orientation, a second end lying inside the trachea of the wearer in the use orientation, a first lumen coupling the first and second ends of the tracheostomy tube and a fenestration through a sidewall of the tracheostomy tube coupling the first lumen to the outside of the tracheostomy tube. The apparatus includes a cannula for insertion into the first lumen from the first end of the tracheostomy tube. The cannula includes a first end lying outside the first end of the tracheostomy tube in the use orientation, a second end lying within the first lumen between the first end of the tracheostomy tube and the fenestration, and a second lumen coupling the first and second ends of the cannula.

Illustratively, the apparatus includes a one-way valve at the second end of the cannula.

According to another aspect of the invention, apparatus is provided for assisting phonation in a wearer of a tracheostomy tube having a first end lying outside the trachea of the wearer in the use orientation, a second end lying inside the trachea of the wearer in the use orientation and a first lumen coupling the first and second ends of the tracheostomy tube. The apparatus includes a cannula for insertion into the first lumen from the first end of the tracheostomy tube. The cannula includes a first end lying outside the first end of the tracheostomy tube in the use orientation, a second end lying adjacent the second end of the tracheostomy tube, a second lumen coupling the first and second ends of the cannula and a one-way valve at the second end of the cannula.

Illustratively, the one-way valve permits the flow of gases from the first end of the cannula to the second end of the cannula when the first end of the cannula is at a higher pressure than the second end of the cannula, but impedes the flow of gases from the second end of the cannula to the first end of the cannula when the second end of the cannula is at a higher pressure than the first end of the cannula.

BRIEF DESCRIPTION OF THE DRAWINGS

The invention may best be understood by referring to the following detailed description and accompanying drawings which illustrate the invention. In the drawings.

DETAILED DESCRIPTION OF ILLUSTRATIVE EMBODIMENTS

Figure 1:
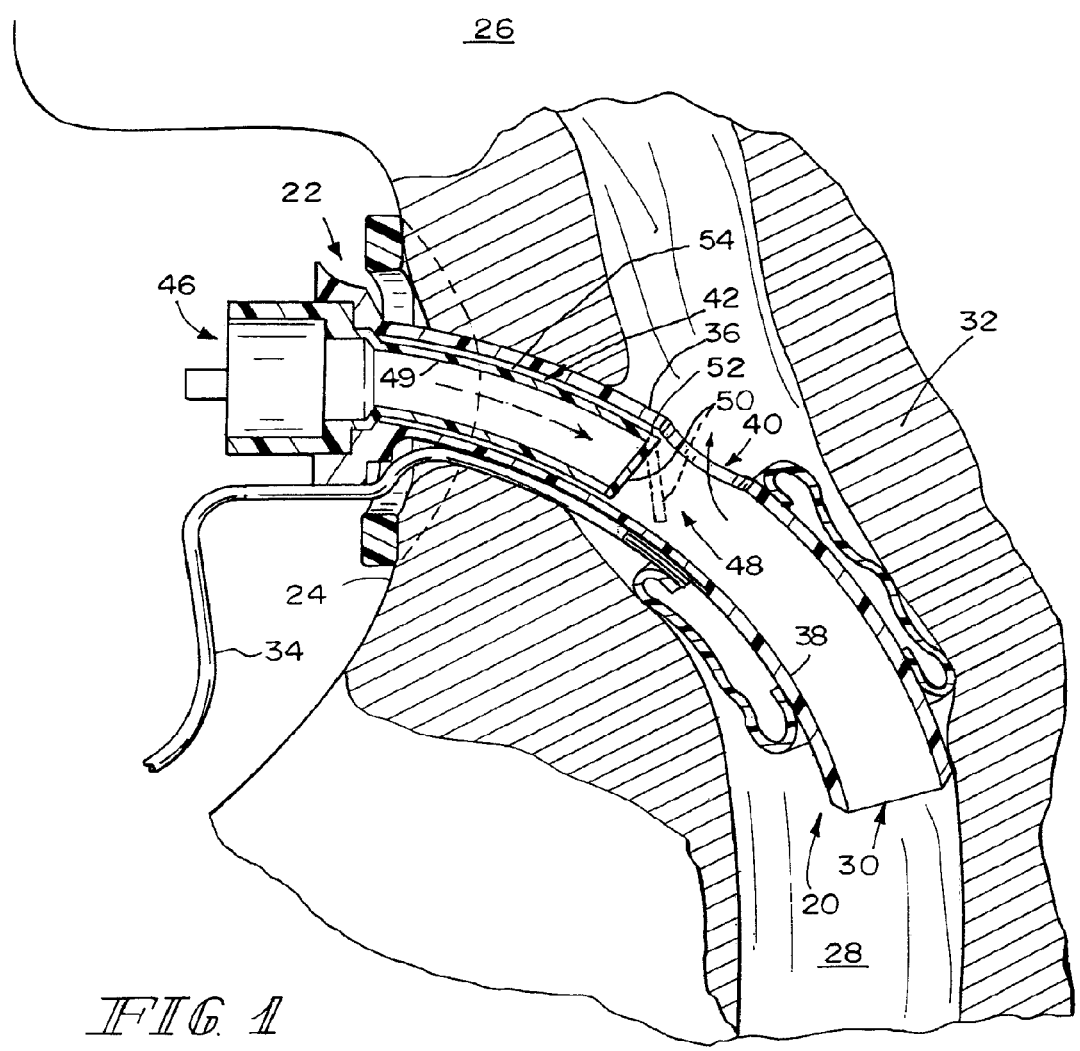
FIG. 1 illustrates a sectional side elevational view of the neck of a wearer of a device constructed according to the invention.
Figure 2:
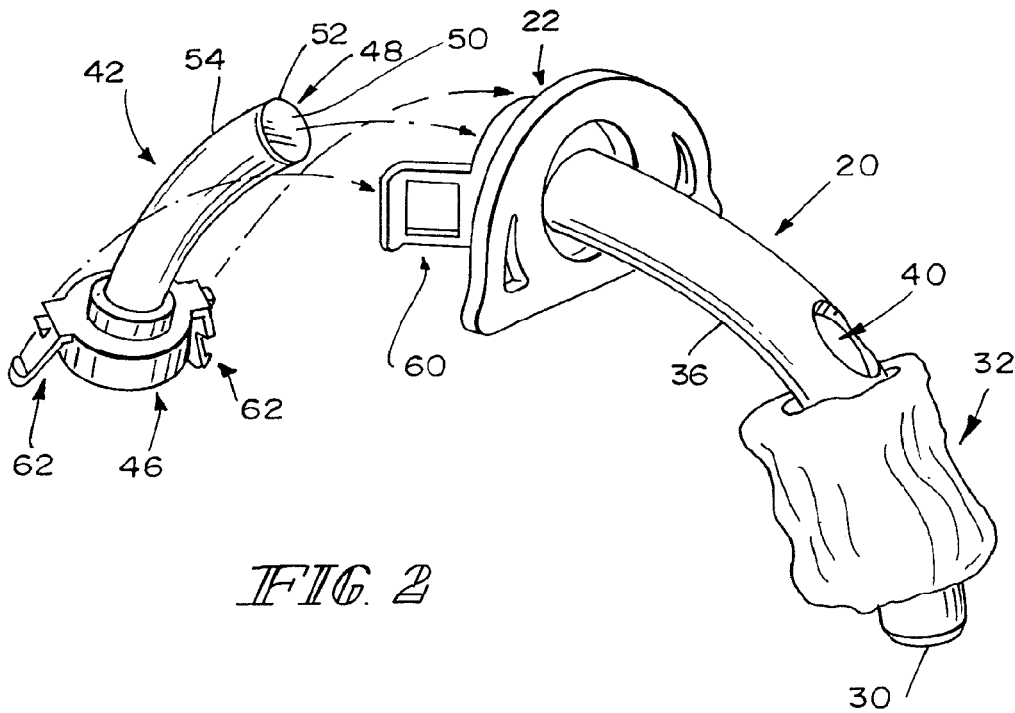
FIG. 2 illustrates a disassembled perspective view of details illustrated in FIG. 1.
Figure 3:
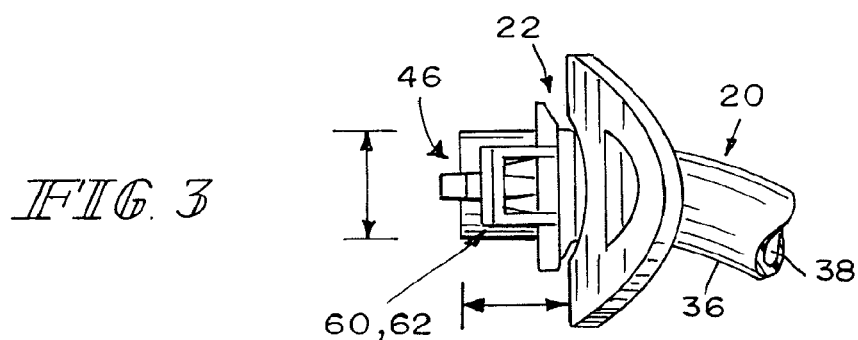
FIG. 3 illustrates a fragmentary side elevational view of certain details of the device illustrated in FIGS. 1-2.

Referring now to FIGS. 1-3, a tracheostomy tube, or outer cannula 20 of the general type described in U.S. Pat. No. 6,722,367 or U.S. published patent application 2007-0144526-A1 has a first outer end 22 which in use resides outside and adjacent the tissue of the front 24 of the neck of a wearer 26. The teachings of U.S. Pat. No. 6,722,367 and U.S. published patent application 2007-0144526-A1 are hereby incorporated herein by reference. This listing is not intended to be a representation that a complete search of all relevant art has been made, or that no more pertinent art than that listed exists, or that the listed art is material to patentability. Nor should any such representation be inferred.

The outer cannula 20 curves rearwardly and downwardly from first end 22 generally in accordance with the anatomy of the trachea 28 through the trachea 28 of the wearer 26 and terminates at a second, distal, tracheal end 30. Some such outer cannulae 20 are provided adjacent their second ends 30 with inflatable cuffs 32 which are inflated and deflated as necessary or desirable through conduits 34 provided for this purpose adjacent, on or in the sidewalls 36 of the outer cannulae 20. However, it is not essential to the present invention that the outer cannula 20 include a cuff 32.

Generally, the outer cannulae include generally circular cross section lumens 38 which extend between ends 22 and 30 and open into the ends providing a passageway through the outer cannula 20. Some such outer cannulae 20 are provided with (a) fenestration(s) 40 between ends 22, 30 through which respiration products escape, as will be described. However, again, it is not essential to the present invention that the outer cannula 20 be provided with such (a) fenestration(s) 40. In U.S. published patent application 2007-0144526-A1, the fenestration(s) 40 is (are) provided as close as reasonably possible to the upper extent of cuff 32, but it is not essential to the practice of the present invention that the fenestration(s) 40 be immediately adjacent the upper extent of cuff 32.

A speaking inner cannula 42 is provided for relatively close fitting insertion through first end 22 into the outer cannula 20 when the wearer 26 wishes to speak. Generally, these devices will find their greatest utility among non-ventilator dependent wearers who wear tracheostomy tubes to maintain their airways patent. However, they are also useful for the ventilator 44 aided wearer 26 during periods when the wearer 26 is not required to be coupled to the ventilator 44. Speaking inner cannula 42 also has a first end 46 which resides outside the neck of the wearer 26 when speaking inner cannula 42 is in a use orientation in outer cannula 20, a second end 48 which resides inside lumen 38 of outer cannula 20 adjacent fenestration(s) 40 when speaking inner cannula 42 is in a use orientation in outer cannula 20, and a lumen 49 coupling the first and second ends 46, 48. Second end 48 of speaking inner cannula 42 is provided with a one-way valve 50 which permits gas flow from the first end 46 toward the second end 48 when the first end 46 is at a higher pressure than the second end 48, but impedes gas flow from the second end 48 toward the first end 46 when the second end is at a higher pressure than the first end 46. The illustrative valve 50 is a flap valve which is hinged at 52 to what is the top of the sidewall 54 of speaking inner cannula 42 when speaking inner cannula 42 is received in lumen 38.

Figure 4:
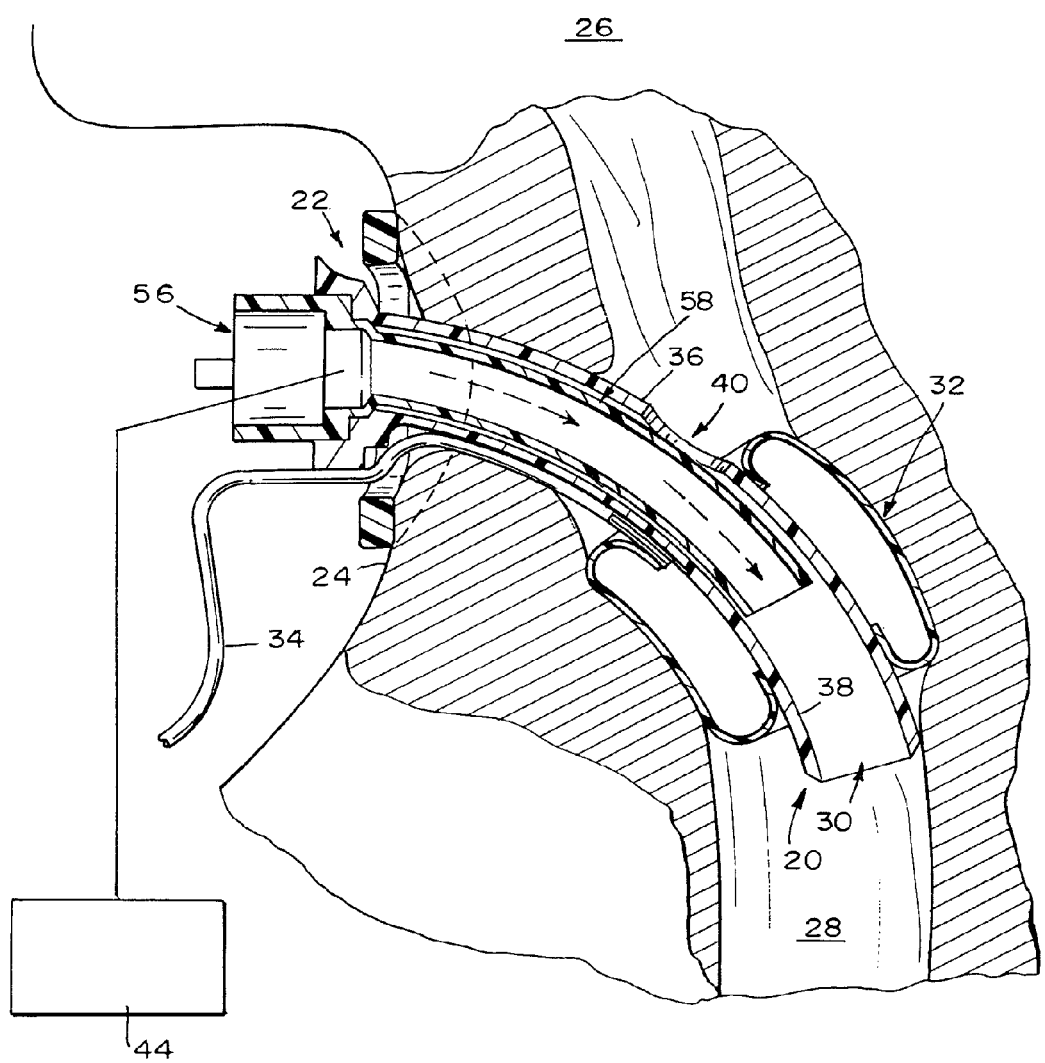
FIG. 4 illustrates a sectional side elevational view of the neck of a wearer of a device useful in understanding the invention.

Referring now particularly to FIG. 4, in use, let it first be assumed that the wearer 26 is one who is on a ventilator 44 at least occasionally. The ventilator 44 may be coupled to a first end 56 of a ventilator inner cannula 58 outside and adjacent the neck of the wearer 26. Such a ventilator inner cannula 58 is also a close fitting inner cannula that extends downward through the lumen 38 past fenestration(s) 40, substantially occluding fenestration(s) 40 and thereby impeding gas flow upward through the fenestration(s) 40 when the ventilator 44 pressurizes the first end 56 of the ventilator inner cannula 58. Air is thereby urged into the lungs of the wearer 26. The ventilator 44 then depressurizes the first end 56 of the ventilator inner cannula 58. The ventilator 44 may draw a slight vacuum on the first end 56 of the ventilator inner cannula 58 in order to draw respiration products out of the wearer 26's lungs. This cycle is repeated as long as the wearer is on the ventilator 44 and has the ventilator inner cannula 58 inserted into his or her outer cannula 20.

Referring now to FIGS. 1-4, let it be assumed that the wearer 26 wants to be removed from the ventilator 44, for example, to talk to a visitor or healthcare worker. Typically, the cuff 32 is deflated. The ventilator 44 is uncoupled from the first end 56 of ventilator inner cannula 58. Ventilator inner cannula 58 is uncoupled from the first end 22 of outer cannula 20, and ventilator inner cannula 58 is withdrawn from first end 22 of outer cannula 20. The speaking inner cannula 42 is inserted into the lumen 38 of outer cannula 20 and the attachment devices 60, 62 of cannulae 20, 42 engaged. These devices 60, 62 may be any of a number of types. Reference is here made to the types of attachment devices illustrated in the cited references as examples of the various types of such devices. The first end 46 of speaking inner cannula 42 lies close to the first end 22 of outer cannula 20.

When the speaking inner cannula 42 is so positioned, the second end 48 of speaking inner cannula 42 lies adjacent and upstream (that is, toward first ends 22, 46 of the outer and inner cannulae 20, 42, respectively) of fenestration(s) 40. When the wearer 26 inhales, air is drawn through first end 46 of speaking inner cannula 42, downward through valve 50, through the remaining length of lumen 38 and into the lungs of the wearer 26. When the wearer 26 exhales, air flows upward through lumen 38 until it reaches fenestration(s) 40. One-way valve 50 closes, forcing the respiration products upward through fenestration(s) 40 and upward through the larynx of the wearer 26 permitting phonation. When the wearer 26 wants to go back on the ventilator 44, speaking inner cannula 42 is removed, ventilator inner cannula 58 is reinserted in lumen 38 and reattached 60, 62 to outer cannula 20 and ventilator 44 and ventilator 44-assisted respiration resumes.

Figure 5:
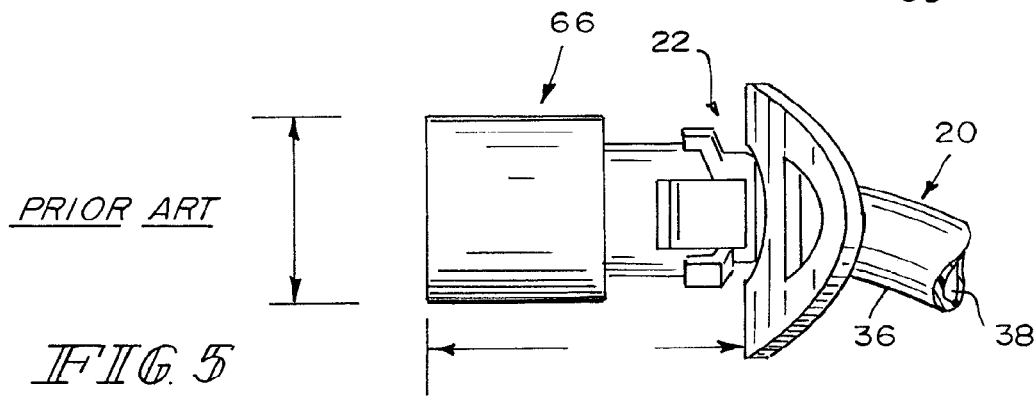
FIG. 5 illustrates a fragmentary side elevational view of certain details of a prior art device useful in understanding the invention.

Fingertip occlusion of the outer end of the cannula to enable speech is thus eliminated. With reference to FIG. 5 for comparison, the prior art one-way valve 66 that projects out beyond the outer end 22 of the tracheostomy tube 20 is also eliminated.

Figure 6:
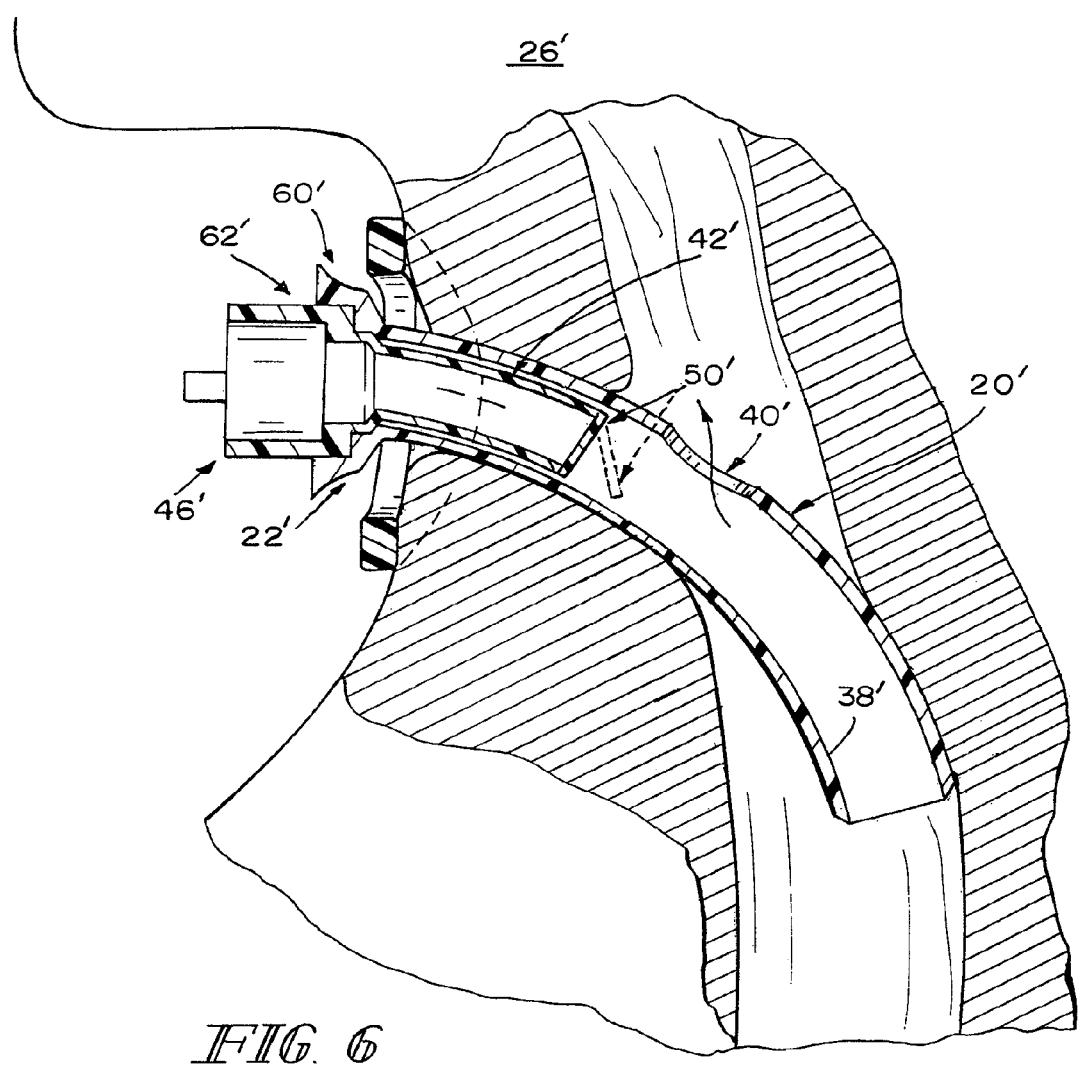
FIG. 6 illustrates a sectional side elevational view of the neck of a wearer of another device constructed according to the invention; and, FIG. 7 illustrates a sectional side elevational view of the neck of a wearer of yet another device constructed according to the invention.

Referring now particularly to FIG. 6, let it be assumed that the wearer 26' is not ventilator-dependent, but rather, requires the outer cannula 20' to maintain an airway. Typically, such cannulae 20' do not have cuffs such as cuff 32 of the outer cannula 20 of FIGS. 1-4. The speaking inner cannula 42' is inserted into the lumen 38' of outer cannula 20' and the attachment devices 60', 62' of cannulae 20', 42' engaged. The first end 46' of speaking inner cannula 42' lies close to the first end 22' of outer cannula 20'. When the wearer 26' inhales, air is drawn through first end 46' of speaking inner cannula 42', downward through valve 50', through the remaining length of lumen 38' and into the lungs of the wearer 26'. When the wearer 26' exhales, air flows upward through lumen 38' until it reaches fenestration(s) 40'. One-way valve 50' closes, forcing the respiration products upward through fenestration(s) 40' and upward through the larynx of the wearer 26' permitting phonation.

Figure 7:
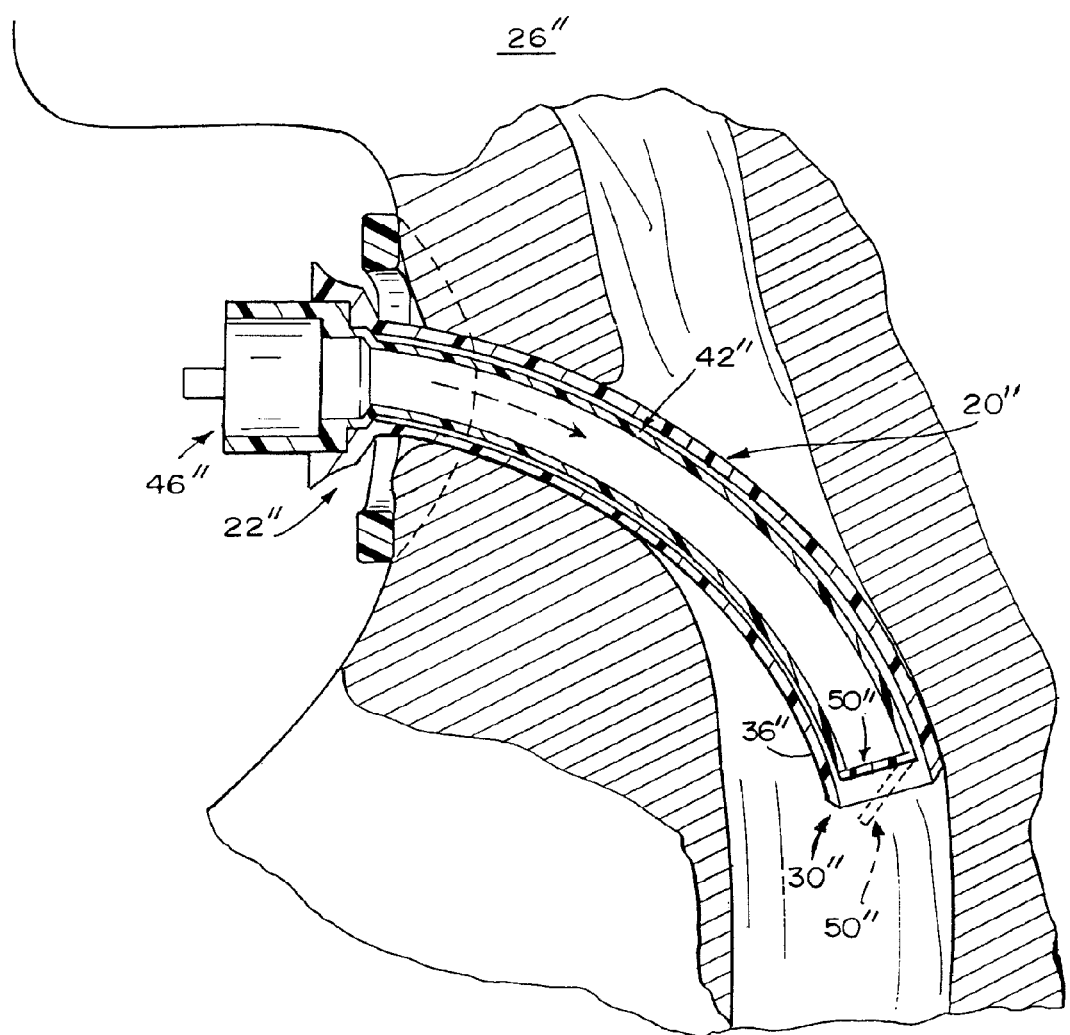

Referring now particularly to FIG. 7, in another embodiment, again, the wearer 26" is not ventilator dependent, but only requires the outer cannula 20" to keep his or her airway patent. This outer cannula 20" is not provided with either (a) fenestration(s), such as fenestration 40 of the embodiment of FIGS. 1-4 or fenestration 40' of the embodiment of FIG. 6, along its length intermediate its first 22" and second 30" ends, or with a cuff, such as cuff 32 of the embodiment of FIGS. 1-4. The speaking inner cannula 42" in this embodiment extends substantially the full length of the outer cannula 20", placing the one-way valve 50" in this embodiment adjacent the second end 30" of outer cannula 20". In this embodiment for non-ventilator dependent wearer 26", when the wearer 26" inhales, air is drawn through first end 46" of speaking inner cannula 42", downward through one-way valve 50", and into the lungs of the wearer 26". When the wearer 26" exhales, one-way valve 50" closes, forcing the respiration products upward around the cuffless outer sidewall 36" of outer cannula 20" and upward through the larynx of the wearer 26" permitting phonation.

What is claimed is:

1. Apparatus for assisting phonation in a wearer of a tracheostomy tube having a first end lying outside the trachea of the wearer in the use orientation, a second end lying inside the trachea of the wearer in the use orientation, a first lumen coupling the first and second ends of the tracheostomy tube and a fenestration through a sidewall of the tracheostomy tube coupling the first lumen to the outside of the tracheostomy tube, the apparatus including a cannula for insertion into the first lumen from the first end of the tracheostomy tube, the cannula including a first end lying outside the first end of the tracheostomy tube in the use orientation, a second end lying within the first lumen adjacent and toward the first end of the tracheostomy tube from the fenestration, and a second lumen coupling the first and second ends of the cannula, a one-way valve at the second end of the cannula, the second end of the cannula being positioned toward the first end of the tracheostomy tube from the fenestration when the cannula is in the use orientation in the tracheostomy tube, the one-way valve permitting the flow of gases from the first end of the cannula to the second end of the cannula when the first end of the cannula is at a higher pressure than the second end of the cannula, but impeding the flow of gases from the second end of the cannula to the first end of the cannula when the second end of the cannula is at a higher pressure than the first end of the cannula.

2. Apparatus for assisting phonation in a wearer of a tracheostomy tube having a first end lying outside the trachea of the wearer in the use orientation, a second end lying inside the trachea of the wearer in the use orientation, a first lumen coupling the first and second ends of the tracheostomy tube and a fenestration through a sidewall of the tracheostomy tube coupling the first lumen to the outside of the tracheostomy tube, the apparatus including a cannula for insertion into the first lumen from the first end of the tracheostomy tube, the cannula including a first end lying outside the first end of the tracheostomy tube in the use orientation, a second end lying within the first lumen adjacent and toward the first end of the tracheostomy tube from the fenestration, and a second lumen coupling the first and second ends of the cannula, a one-way valve at the second end of the cannula, the one-way valve permitting the flow of gases from the first end of the cannula to the second end of the cannula when the first end of the cannula is at a higher pressure than the second end of the cannula, but impeding the flow of gases from the second end of the cannula to the first end of the cannula when the second end of the cannula is at a higher pressure than the first end of the cannula.

3. Apparatus for assisting phonation in a wearer of a tracheostomy tube having a first end lying outside the trachea of the wearer in the use orientation, a second end lying inside the trachea of the wearer in the use orientation, a first lumen coupling the first and second ends of the tracheostomy tube and a fenestration through a sidewall of the tracheostomy tube coupling the first lumen to the outside of the tracheostomy tube, the apparatus including a cannula for insertion into the first lumen from the first end of the tracheostomy tube, the cannula including a first end lying outside the first end of the tracheostomy tube in the use orientation, a second end lying within the first lumen between the first end of the tracheostomy tube and the fenestration, and a second lumen coupling the first and second ends of the cannula, a one-way valve at the second end of the cannula, the one-way valve permitting the flow of gases from the first end of the cannula to the second end of the cannula when the first end of the cannula is at a higher pressure than the second end of the cannula, but impeding the flow of gases from the second end of the cannula to the first end of the cannula when the second end of the cannula is at a higher pressure than the first end of the cannula.

4. Apparatus for assisting phonation in a wearer of a tracheostomy tube having a first end lying outside the trachea of the wearer in the use orientation, a second end lying inside the trachea of the wearer in the use orientation and a first lumen coupling the first and second ends of the tracheostomy tube, the apparatus including a cannula for insertion into the first lumen from the first end of the tracheostomy tube, the cannula including a first end lying outside the first end of the tracheostomy tube in the use orientation, a second end adjacent the second end of the tracheostomy tube, a second lumen coupling the first and second ends of the cannula and a one-way valve at the second end of the cannula, the one-way valve permitting the flow of gases from the first end of the cannula to the second end of the cannula when the first end of the cannula is at a higher pressure than the second end of the cannula, but impeding the flow of gases from the second end of the cannula to the first end of the cannula when the second end of the cannula is at a higher pressure than the first end of the cannula.

* * * * *